United States Patent
Giles et al.

(10) Patent No.: US 10,083,824 B2
(45) Date of Patent: Sep. 25, 2018

(54) ION MOBILITY SPECTROMETRY DATA DIRECTED ACQUISITION

(71) Applicant: Micromass UK Limited, Wilmslow (GB)

(72) Inventors: Kevin Giles, Stockport (GB); Martin Raymond Green, Bowdon (GB); Steven Derek Pringle, Darwen (GB); Keith Richardson, High Peak (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/317,045

(22) PCT Filed: Jun. 11, 2015

(86) PCT No.: PCT/GB2015/000173
§ 371 (c)(1),
(2) Date: Dec. 7, 2016

(87) PCT Pub. No.: WO2015/189545
PCT Pub. Date: Dec. 17, 2015

(65) Prior Publication Data
US 2017/0140908 A1    May 18, 2017

(30) Foreign Application Priority Data

Jun. 11, 2014 (GB) .................................. 1410379.0
Dec. 15, 2014 (EP) .................................. 14198042
Dec. 15, 2014 (GB) .................................. 1422289.7

(51) Int. Cl.
*H01J 49/00* (2006.01)
*G01N 27/62* (2006.01)

(52) U.S. Cl.
CPC ........ *H01J 49/0031* (2013.01); *G01N 27/622* (2013.01); *H01J 49/0045* (2013.01)

(58) Field of Classification Search
CPC .... H01J 49/0031; H01J 49/0045; H01J 49/26; H01J 49/0027; H01J 49/02; G01N 27/622
(Continued)

(56) References Cited

U.S. PATENT DOCUMENTS 7,622,711 B2   11/2009   Wildgoose et al.
8,168,943 B2    5/2012   Schwartz et al.
(Continued)

FOREIGN PATENT DOCUMENTS

GB   2513973   11/2014
GB   2514455   11/2014
(Continued)

OTHER PUBLICATIONS

"Synapt-G2-S—The Things You Cannot See Can Change Everything", http://www.elta90.com/wp-content/uploads/2011/08/SYNAPT-G2-S-Brochure.pdf, retrieved Aug. 2015.
(Continued)

Primary Examiner — Nicole Ippolito

(57) ABSTRACT

A method of analyzing ions, comprising performing an initial multidimensional survey scan comprising separating parent ions according to a first physico-chemical property and separating said parent ions according to a second physico-chemical property, producing a two-dimensional data set comprising data corresponding to said first physico-chemical property and data corresponding to said second physico-chemical property, identifying one or more target ion species of interest and determining a mode of operation of a mass spectrometer for said target ion species of interest using data relating to said target ion species of interest in said two-dimensional data set, wherein said mode of opera-
(Continued)

tion comprises the location of fragmentation of said target ions of interest.

14 Claims, 2 Drawing Sheets

(58) Field of Classification Search
USPC .................................................. 250/281, 282
See application file for complete search history.

(56) References Cited

U.S. PATENT DOCUMENTS

| | | | |
|---|---|---|---|
| 8,278,620 B2 | 10/2012 | Schwartz et al. | |
| 8,694,264 B2 | 4/2014 | Kajihara et al. | |
| 9,202,678 B2 | 12/2015 | Dantus et al. | |
| 9,305,762 B2 | 4/2016 | Covey et al. | |
| 9,478,405 B2 | 10/2016 | Coon et al. | |
| 9,576,777 B2 | 2/2017 | Giles et al. | |
| 2015/0233866 A1* | 8/2015 | Verenchikov ........ | G01N 27/622 250/282 |
| 2016/0054264 A1 | 2/2016 | Carver et al. | |

FOREIGN PATENT DOCUMENTS

| | | |
|---|---|---|
| WO | 2013/140132 | 9/2013 |
| WO | 2014/140542 | 9/2014 |

OTHER PUBLICATIONS

Pringle et al., "*An Investigation of the Mobility Separation of Some Peptide and Protein Ions Using a New Hybrid Quadrupole/Travelling Wave IMS/oa-ToF Instrument*", International Journal of Mass Spectrometry, vol. 261, No. 1, pp. 1-12, (Feb. 2007).

Elviri, L., "*ETD and ECM Mass Spectrometry Fragmentation for the Characterization of Protein Post Translation Modifications*", Tandem Mass Spectrometry—Applications and Principles, pp. 161-178 (Feb. 2012).

Wickramasekara S. et al., "*Electrospray Quadrupole Travelling Wave Ion Mobility Time-of-Flight Mass Spectrometry for the Detection of Plasma Metabolome Changes Caused by Xanthohumol in Obese Zucker (fa/fa) Rats*", Metabolites, vol. 3, pp. 707-717, (Aug. 2013).

Haller, I. et al., "*Collision Induced Decomposition of Peptides. Choice of Collision Parameters*", Journal of the American Society for Mass Spectrometry, vol. 7, No. 7, pp. 677-681, (Jul. 1996).

* cited by examiner

ION MOBILITY SPECTROMETRY DATA DIRECTED ACQUISITION

CROSS-REFERENCE TO RELATED APPLICATIONS

This application represents the U.S. National Phase of International Application number PCT/GB2015/000173 entitled "Ion Mobility Spectrometry Data Directed Acquisition" filed 11 Jun. 2015, which claims priority from and the benefit of United Kingdom patent application No. 1410379.0 filed 11 Jun. 2014, United Kingdom patent application No. 1422289.7 filed 15 Dec. 2014 and European patent application No. 14198042.5 filed 15 Dec. 2014. The entire contents of these applications are incorporated herein by reference.

FIELD OF THE PRESENT INVENTION

The present invention relates generally to mass spectrometry and in particular to methods of analysing ions and analytical instruments for analysing ions.

BACKGROUND

Data directed analysis or acquisitions ("DDA") has long been established as a useful tool for the analysis of complex mixtures due to the added specificity of the mass filtering step. More recently, ion mobility spectrometry ("IMS") based separations, when combined with mass separations with and without fragmentation, has also shown benefits for the analysis of such complex mixtures. This is due to the increased peak capacity resulting from, for example, the partial orthogonality of ion mobility and mass to charge ratio.

It has been shown how the combination of IMS with a quadrupole mass filter, a fragmentation device and a Time of Flight ("ToF") mass analyser can improve the specificity, selectivity and duty cycle of tandem mass spectrometry experiments.

Reference is made to WO 2013/40132 (Micromass) and GB-2505265 (Micromass) which disclose multi-dimensional survey scans for improved data dependent acquisitions.

GB-2514455 (Micromass) discloses data dependent control of the intensity of ions separated in multiple dimensions.

GB-2513973 discloses a DDA experiment with reduced data processing.

WO 2008/025014 (Schwartz) discloses data-dependent selection of dissociation type in a mass spectrometer.

It is desired to provide an improved method of analysing ions.

SUMMARY

According to an aspect of the present disclosure there is provided a method of analysing ions comprising:

performing an initial multidimensional survey scan comprising separating parent ions according to a first physico-chemical property and separating the parent ions according to a second physico-chemical property;

producing a two-dimensional data set comprising data corresponding to the first physico-chemical property and data corresponding to the second physico-chemical property;

identifying one or more target ion species of interest; and determining a mode of operation of a mass spectrometer for the target ion species of interest using data relating to the target ion species of interest in the two-dimensional data set, wherein the mode of operation comprises the location or position of fragmentation of the target ions of interest.

The approach according to various embodiments is distinct from conventional methods such as that disclosed in GB-251973 (Micromass) which does not disclose or suggest using the location of an ion species in two-dimensional space to determine a location of fragmentation within a mass spectrometer.

The approach according to various embodiments further differs from the arrangement disclosed in WO 2013/140132 (Micromass) in that data relating to a target ion species of interest may be identified in the two-dimensional data set and used to calculate a mode of operation for the target ion species of interest. In the approach disclosed in WO 2013/140132 (Micromass), a two-dimensional data set is used only to identify ions of interest and not to calculate a mode of operation.

The location or position may refer to the location or position of fragmentation within a mass spectrometer, for example the geometry of the mass spectrometer. For example, it may be determined that fragmentation of the target ion species is to occur prior to, or after passing ions through or into a device based on the position of the target ion species of interest in the two-dimensional data set. The device may comprise an ion trap, ion guide or ion mobility spectrometer or separator.

The mode of operation may further comprise a mode of fragmentation. For example, it may be determined that fragmentation of the target ion species is to comprise Electron Transfer Dissociation and/or Collision Induced Dissociation and/or Electron Capture Dissociation based on the position of the target ion species of interest in the two-dimensional data set. The mode of fragmentation may be determined in addition to the location or position of the fragmentation as described herein.

The method may further comprise switching to the mode of operation when analysing the target ion species.

The method may further comprise determining a presence of chimeric interference in the one or more target ion species, or product or fragment ions derived from the one or more target ion species, from the two-dimensional data set.

The method may further comprise:

separating ions according to their ion mobility and/or selecting ions based on their mass to charge ratio; and/or fragmenting the target ion species to produce fragment or product ions.

The step of fragmenting ions may be performed before or after the step of separating and/or selecting ions if a presence of chimeric interference in the one or more target ion species, or product or fragment ions derived from the one or more target ion species, is determined from the two-dimensional data set.

The step of fragmenting ions may be performed before or after the step of separating and/or selecting ions if no presence of chimeric interference in the one or more target ion species, or product or fragment ions derived from the one or more target ion species, is determined from the two-dimensional data set.

The step of fragmenting ions may be performed before or after the step of separating and/or selecting ions if a presence of chimeric interference in the one or more target ion species, or product or fragment ions derived from the one or more target ion species, is determined from the two-dimensional data set, and a level of said chimeric interference is above a predetermined amount.

The step of fragmenting ions may be performed before or after the step of separating and/or selecting ions if a presence of chimeric interference in the one or more target ion species, or product or fragment ions derived from the one or more target ion species, is determined from the two-dimensional data set, and a level of said chimeric interference is below a predetermined amount.

The method may further comprise calculating an operating parameter for the target ions species using data related to the target ion species in the two-dimensional data set.

The method may further comprise applying the operating parameter when analysing the target ion species.

The operating parameter may comprise one or more of collision energy, reaction time and attenuation factor.

The step of calculating an operating parameter may comprise optimising the operating parameter for the target ion species using data relating to the target ion species of interest in the two-dimensional data set.

The step of determining a mode of operation may comprise determining the most suitable or effective fragmentation mode of operation for the target ion species.

The mode of operation may comprise one or more of an Electron Transfer Dissociation mode of operation, a Collision Induced Dissociation mode of operation and an Electron Capture Dissociation mode of operation.

The method may further comprise determining a charge state of the target ion species using data relating to the target ion species of interest in the two-dimensional data set. The method may further comprise switching to a Collision Induced Dissociation mode of operation when analysing the target ion species based on the determining a charge state of the target ion species.

The first physico-chemical property may comprise one or more of ion mobility, differential ion mobility, Collision Cross Section ("CCS"), drift time, mass, mass to charge ratio and time of flight; and/or The second physico-chemical property may comprise one or more of ion mobility, differential ion mobility, Collision Cross Section ("CCS"), drift time, mass, mass to charge ratio and time of flight.

According to an aspect of the present disclosure there is provided a method of mass spectrometry comprising a method of analysing ions as disclosed above.

According to an aspect of the present disclosure there is provided an analytical instrument for analysing ions comprising:

a first separator or filter for separating or filtering ions according to a first physico-chemical property;

a second separator or filter for separating or filtering ions according to a second physico-chemical property; and a control system arranged and adapted:

(i) to perform an initial multi-dimensional survey scan comprising separating parent ions according to the first physico-chemical property using the first separator and separating the parent ions according to the second physico-chemical property using the second separator;

(ii) to produce a two-dimensional data set comprising data corresponding to the first physico-chemical property and data corresponding to the second physico-chemical property;

(iii) to identify one or more target ion species of interest; and (iv) to determine a mode of operation of a mass spectrometer for the target ion species of interest using data relating to the target ion species of interest in the two-dimensional data set, wherein the mode of operation comprises the location of fragmentation of the target ions of interest.

According to an aspect of the present disclosure there is provided a mass spectrometer comprising an analytical instrument for analysing ions as disclosed above.

According to an aspect of the present invention there is provided a method of analysing ions comprising:

performing an initial multidimensional survey scan comprising separating parent ions according to a first physico-chemical property and separating the parent ions according to a second physico-chemical property;

producing a two-dimensional data set comprising data corresponding to the first physico-chemical property and data corresponding to the second physico-chemical property;

identifying one or more target ion species of interest; and calculating an operating parameter and/or determining a mode of operation of a mass spectrometer for the target ion species of interest using data relating to the target ion species of interest in the two-dimensional data set.

The operating parameter may comprise a fragmentation parameter and/or the mode of operation may comprise a mode of fragmentation.

The method may further comprise switching to the mode of operation when analysing the target ion species.

The method may further comprise applying or using the operating parameter when analysing the target ion species.

The operating parameter may comprise one or more of collision energy, reaction time, attenuation factor and fragmentation location.

The mode of operation may comprise one or more of an Electron Transfer Dissociation mode of operation, a Collision Induced Dissociation mode of operation and an Electron Capture Dissociation mode of operation.

The step of calculating an operating parameter or mode of operation may comprise optimising the operating parameter or mode of operation for the target ion species using data relating to the target ion species of interest in the two-dimensional data set.

The step of determining a mode of operation may comprise determining the most suitable or effective fragmentation mode of operation for the target ion species.

The method may further comprise determining a charge state of the target ion species using data relating to the target ion species of interest in the two-dimensional data set.

The method may further comprise switching to a Collision Induced Dissociation mode of operation when analysing the target ion species based on the determining a charge state of the target ion species, for example a low charge state and/or where the target ion species contains singly-charged ions.

The method may further comprise determining a presence of chimeric interference in the one or more target ion species, or product or fragment ions derived from the one or more target ion species, from the two-dimensional data set.

The method may further comprise:

separating ions according to their ion mobility and/or selecting ions based on their mass to charge ratio; and optionally fragmenting the target ion species to produce fragment or product ions.

The step of fragmenting ions may be performed before or after the step of separating and/or selecting ions.

The step of fragmenting ions may be performed after the step of separating and/or selecting ions if a presence of chimeric interference in the one or more target ion species, or product or fragment ions derived from the one or more target ion species, is determined from the two-dimensional data set.

The mode of operation may comprise the location of fragmentation of the target ions of interest.

The first physico-chemical property may comprise one or more of ion mobility, differential ion mobility, Collision Cross Section ("CCS"), drift time, mass, mass to charge ratio and time of flight.

The second physico-chemical property may comprise one or more of ion mobility, differential ion mobility, Collision Cross Section ("CCS"), drift time, mass, mass to charge ratio and time of flight.

According to an aspect of the present invention there is provided a method of mass spectrometry comprising a method of analysing ions as described above.

According to an aspect of the present invention there is provided an analytical instrument for analysing ions comprising:

a first separator or filter for separating or filtering ions according to a first physico-chemical property;

a second separator or filter for separating or filtering ions according to a second physico-chemical property; and a control system arranged and adapted:

(i) to perform an initial multi-dimensional survey scan comprising separating parent ions according to the first physico-chemical property using the first separator and separating the parent ions according to the second physico-chemical property using the second separator;

(ii) to produce a two-dimensional data set comprising data corresponding to the first physico-chemical property and data corresponding to the second physico-chemical property;

(iii) to identify one or more target ion species of interest; and (iv) to calculate an operating parameter and/or determine a mode of operation of a mass spectrometer for the target ion species of interest using data relating to the target ion species of interest in the two-dimensional data set.

According to an aspect of the present invention there is provided a mass spectrometer comprising the analytical instrument for analysing ions as described above.

According to an aspect of the present disclosure there is provided an apparatus for ion mobility and/or mass spectrometry comprising:

separating a population of ions according to their ion mobility;

further separating said ions by mass to charge ratio in a time of flight mass analyser;

wherein, in use, the time of flight mass analyser samples the ion population multiple times during a single ion mobility spectrometry separation cycle, and the method further comprises:

producing a two-dimensional data set based on Collision Cross Section ("CCS") and/or drift time and/or mass to charge ratio and/or time of flight;

identifying components of interest based on their location within the two-dimensional data set; and controlling mass spectrometer devices and further analysing components of interest.

The mass spectrometer device may comprise a quadrupole mass filter.

The step of further analysis may comprise fragmenting or reacting ions of interest to produce associated product ions.

The determination of ions of interest may be based on comparisons with component lists containing Collision Cross Sections ("CCS") and/or drift times and/or mass to charge ratios and/or times of flight determined or generated previously.

The determination of ions of interest may be based on component lists containing Collision Cross Sections ("CCS") and/or drift times and/or mass to charge ratios and/or times of flight determined or generated in real time.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions;

and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments of the present disclosure will now be described, together with examples given for illustrative purposes only, by way of example only, and with reference to the accompanying drawings in which.

DETAILED DESCRIPTION

Figure 1:
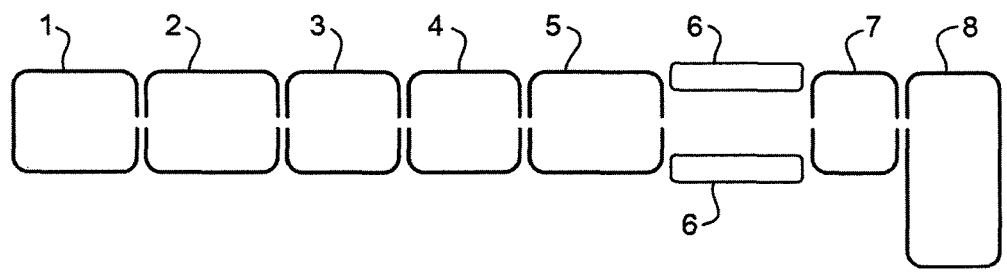
FIG. 1 shows a geometry of a mass spectrometer.
Figure 2:
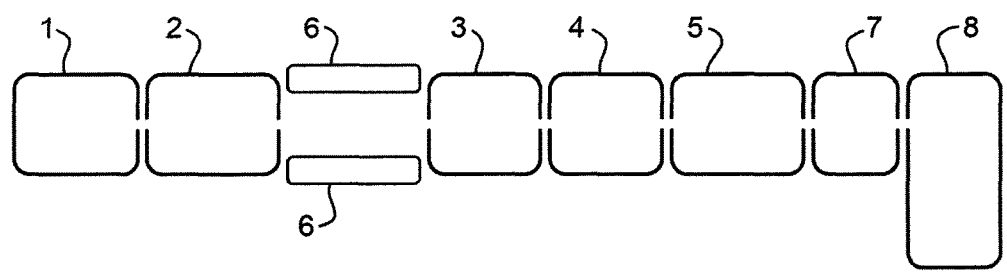
FIG. 2 shows a geometry of a mass spectrometer.

FIGS. 1 and 2 show schematics of two geometries of a mass spectrometer.

FIG. 1 shows an ion mobility spectrometer 4 which may form part of the source region in a geometry optionally comprising an ion mobility spectrometer 4 ("IMS"), a downstream quadrupole mass filter 6 ("Q") and a downstream Time of Flight mass analyser 8 ("ToF") similar to the arrangement disclosed, for example, in WO 2013/140132 (Micromass).

In FIG. 2 the ion mobility spectrometer 4 is optionally arranged downstream of the quadrupole mass filter 6, as seen, for example, in commercial SYNAPT (RTM) Q-IMS-ToF geometries.

The geometries shown in FIGS. 1 and 2 allow the acquisition of a two-dimensional nested mass to charge ratio and drift time data set.

Figure 3:
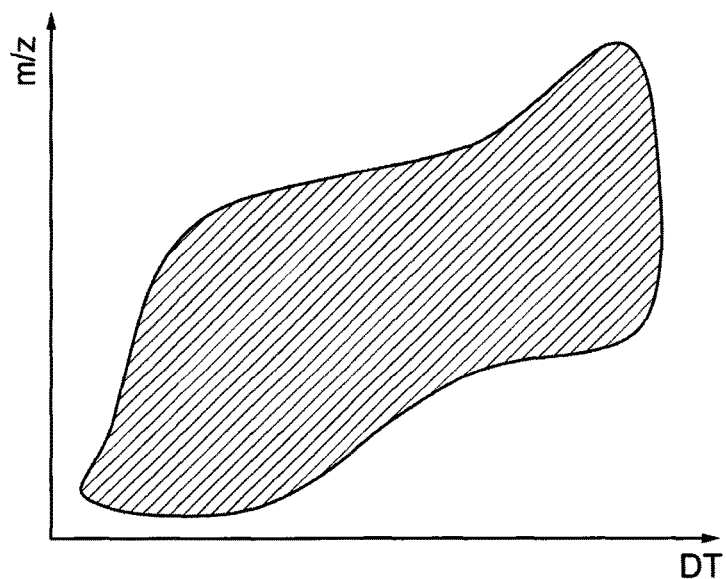
FIG. 3 shows a graph depicting a two-dimensional data set.

FIG. 3 shows a schematic of the type of data which may be obtained from these geometries which optionally has two axes corresponding to mass to charge ratio and drift time. These axes could be interchanged with time of flight, Collision Cross Section ("CCS") or ion mobility respectively, or any combination thereof, optionally by means of calibrating or uncalibrating a relationship between time and the physico-chemical properties of, for example, mass to charge ratio, CCS or ion mobility.

Components may be identified within the two-dimensional data set and it may be determined whether or not they are of interest, and optionally whether or not to isolate the components using the quadrupole mass filter. Methods of determining whether components are of interest may be performed, for example, by comparing with a list or database. Such a list or database may be generated in real time and optionally based on data obtained from previous scans in the experiment. Alternatively, or additionally, a or the list may be based on previous experiments or steps, for example a method development experiment or step. The comparison with the list can take the form of an include list and/or database, where specific precursor components may be effectively targeted, or an exclude list where specific precursor components may be avoided.

Figure 4:
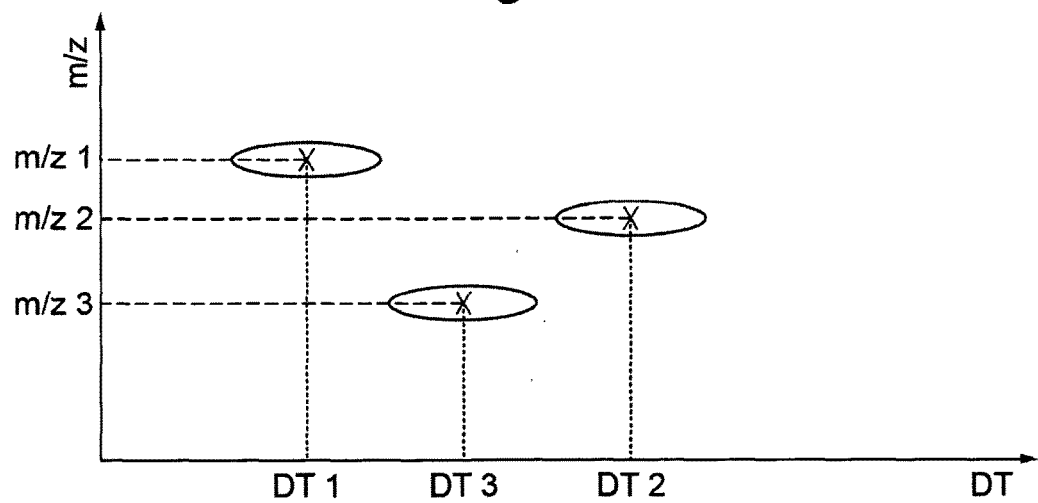
FIG. 4 shows a graph depicting a two-dimensional data set.

FIG. 4 shows a zoomed in representation of components in a two-dimensional space. Components may be identified and a centroid accurate mass to charge ratio and drift time may be associated with each component. These values of mass to charge ratio and drift time (or CCS or ion mobility) together with, for example, chromatographic elution time, may be compared with previously described list or lists, for example as generated above. A centroid may not be necessary and a peak top or apex assignment may suffice.

It is possible to use the above approach to optionally improve instrument functions such as fragmentation or reaction control where component positions in the two-dimensional space may allow optimisation of the collision energy or reaction time.

For example, the position of the ions of interest in the two-dimensional space may be used to optimise the subsequent fragmentation of target ions of interest. The optimisation of the fragmentation process optionally includes optimisation of collision energy for Collision Induced Dissociation ("CID"). The position in the two-dimensional space optionally includes information related to the mass to charge ratio and/or charge state and/or structure of ions, all of which can have an effect on the optimum collision energy. Similar approaches can be adopted for other fragmentation techniques such as Electron Transfer Dissociation ("ETD"), Electron Capture Dissociation ("ECD") and Proton Transfer Reactions ("PTR") where the information related to the position in the two-dimensional space can be used to optimise the reaction times.

The position of ions in the two-dimensional space may be used in determining which fragmentation technique or mode of fragmentation to use. For example, it is known that ETD may be inefficient for low charge states, for example singly charged ions. The location in the two-dimensional space can be used to identify these ions and the instrument can then optionally be arranged to perform CID of these ions rather than attempting to perform an inefficient ETD like experiment.

Various embodiments of the present disclosure will now be described.

According to an embodiment, the relative position of ions of interest in the two-dimensional space may be used to inform a fragmentation location or mode of fragmentation within an instrument geometry. For example, in instrument geometries where it is possible to fragment both before and after an IMS device, the information in a two-dimensional space may be used to help decide which location to use.

This decision may be based on the presence of chimeric precursor interference. In this context a chimeric precursor interference may comprise a precursor ion that is close enough in mass to charge ratio to a precursor ion of interest so that it will also be transmitted through a mass filter during the precursor isolation step. This can lead to mixing of fragment ions from both (or more) precursor ion fragments which may reduce the likelihood of correctly identifying the component of interest.

The relative positions of the precursor ions in the two-dimensional space can be used to determine if the precursor ions should undergo further or additionally separation in the IMS device before fragmentation. This may alleviate the issues associated with mixing fragment ions from different precursor ions and/or may assist in determining whether or not to fragment ions prior to the IMS device, enabling established high duty cycle time of flight modes ("HDC").

Thus, the relative position of components of interest to chimeric interferences may be used to determine the position of fragmentation within a given geometry. In the presence of chimeric interferences it may be possible to fragment post IMS separation to reduce distraction, whereas the absence of chimeric interferences may indicate it is beneficial to operate before the IMS device and/or with IMS separation of fragment ions and HDC.

The above approaches can also be used to determine the number of stages of fragmentation. For example, based on the data relating to the ions of interest in the two-dimensional data set, it may be determined that fragmentation should occur before or after the IMS device and/or it may be determined that the mass spectrometer or analytical device switches from two stages of fragmentation to a single or no stage(s) of fragmentation.

The data relating to the ions of interest in the two-dimensional data set and/or the position of the ions of interest in the two-dimensional space may be used to determine a fragmentation mode of operation e.g. an Electron Transfer Dissociation mode of operation, a Collision Induced Dissociation mode of operation, an Electron Capture Dissociation mode of operation, a Proton Transfer Reaction mode of operation or a photo-fragmentation mode of operation.

The data relating to the ions of interest in the two-dimensional data set and/or the position of the ions of interest in the two-dimensional space may also indicate the likely charge state of fragment ions. This data may be used to optimise techniques such as high duty cycle time of flight modes where the synchronisation between drift time in an ion mobility spectrometer and time of flight extraction pulse may be charge state dependent.

Similar approaches can also be adopted when determining when to switch between mass spectrometry ("MS"), tandem mass spectrometry ("MS/MS") and ion mobility spectrometry ("IMS") modes. For example, the data relating to the ions of interest in the two-dimensional data set and/or the position of the ions of interest in the two-dimensional space may be used to determine when to switch between MS/MS and MS, or between an IMS-MS/MS mode and an IMS-MS mode, for example Total Ion Current ("TIC") in a region for IMS-MS/MS to MS switch back.

It is also recognised that the approach as disclosed above may be applied in conjunction with a wide range of known ionisation sources and mass analysers although a time of flight mass analyser is the disclosed analyser.

It is also recognised that the approach as disclosed above may be applied with a wide range of instrument control modes including regularly spaced low energy survey scans, regularly spaced high energy survey scans, control modes as described in WO 2013/140132 (Micromass) and combinations thereof.

Whilst various embodiments relate to geometries with a single stage of ion mobility separation, it will be apparent that the approach may also be applied to geometries with more than one stage of ion mobility separation such as IMS-Q-IMS-ToF or Q-IMS-IMS-ToF where fragmentation can occur at multiple stages along the geometry. These geometries can also provide higher than two-dimensional data sets. The use of pre-accumulating IMS devices is also contemplated. It is also recognised that the tandem mass spectrometry scan times can be dynamically chosen based on their position within the two-dimensional data set.

Other separation techniques are also envisaged as benefitting from the above approaches, particularly Differential Mobility Spectrometry ("DMS"), Differential Mobility Analyser ("DMA") and High-Field Asymmetric Waveform Ion Mobility Spectrometry ("FAIMS").

Although the present invention has been described with reference to various embodiments, it will be understood by those skilled in the art that various changes in form and detail may be made without departing from the scope of the disclosure as set forth in the accompanying claims.

The invention claimed is:

1. A method of analysing ions comprising:
    performing an initial multidimensional survey scan comprising separating parent ions according to a first physico-chemical property and separating said parent ions according to a second physico-chemical property;
    producing a two-dimensional data set comprising data corresponding to said first physico-chemical property and data corresponding to said second physico-chemical property;
    identifying one or more target ion species of interest; and
    determining a location of fragmentation within an instrument geometry and/or a mode of fragmentation of a mass spectrometer for said target ion species of interest using data relating to said target ion species of interest in said two-dimensional data set.

2. A method as claimed in claim 1, further comprising switching to fragmenting at said location and/or switching to said mode of fragmentation when analysing said target ion species.

3. A method as claimed in claim 1, further comprising determining a presence of chimeric interference in said one or more target ion species, or product or fragment ions derived from said one or more target ion species, from said two-dimensional data set.

4. A method as claimed in claim 3, further comprising:
    separating ions according to their ion mobility and/or selecting ions based on their mass to charge ratio; and
    fragmenting said target ion species to produce fragment or product ions;

wherein said step of fragmenting ions is performed after said step of separating and/or selecting ions if a presence of chimeric interference in said one or more target ion species, or product or fragment ions derived from said one or more target ion species, is determined from said two-dimensional data set.

5. A method as claimed in claim 1, further comprising calculating an operating parameter for said target ions species using data related to said target ion species in said two-dimensional data set; and applying said operating parameter when analysing said target ion species.

6. A method as claimed in claim 5, wherein said operating parameter comprises one or more of collision energy, reaction time and attenuation factor.

7. A method as claimed in claim 5, wherein the step of calculating an operating parameter comprises optimising said operating parameter for said target ion species using data relating to said target ion species of interest in said two-dimensional data set; and/or the step of determining a mode of operation comprises determining the most suitable or effective fragmentation mode of operation for the target ion species.

8. A method as claimed in claim 1, wherein said mode of operation comprises one or more of an Electron Transfer Dissociation mode of operation, a Collision Induced Dissociation mode of operation and an Electron Capture Dissociation mode of operation.

9. A method as claimed in claim 1, further comprising determining a charge state of said target ion species using data relating to said target ion species of interest in said two-dimensional data set.

10. A method as claimed in claim 9, further comprising switching to a Collision Induced Dissociation mode of operation when analysing said target ion species based on said determining a charge state of said target ion species.

11. A method as claimed in claim 1, wherein said first physico-chemical property comprises one or more of ion mobility, differential ion mobility, Collision Cross Section ("CCS"), drift time, mass, mass to charge ratio and time of flight; and/or wherein said second physico-chemical property comprises one or more of ion mobility, differential ion mobility, Collision Cross Section ("CCS"), drift time, mass, mass to charge ratio and time of flight.

12. A method of mass spectrometry comprising a method of analysing ions as claimed in claim 1.

13. An analytical instrument for analysing ions comprising:

a first separator or filter for separating or filtering ions according to a first physico-chemical property;

a second separator or filter for separating or filtering ions according to a second physico-chemical property; and a control system arranged and adapted:

(i) to perform an initial multi-dimensional survey scan comprising separating parent ions according to said first physico-chemical property using said first separator and separating said parent ions according to said second physico-chemical property using said second separator;

(ii) to produce a two-dimensional data set comprising data corresponding to said first physico-chemical property and data corresponding to said second physico-chemical property;

(iii) to identify one or more target ion species of interest; and (iv) to determine a location of fragmentation within an instrument geometry and/or a mode of fragmentation of a mass spectrometer for said target ion species of interest using data relating to said target ion species of interest in said two-dimensional data set.

14. A mass spectrometer comprising an analytical instrument for analysing ions as claimed in claim 13.

* * * * *